United States Patent
Hwang et al.

(10) Patent No.: US 8,153,167 B2
(45) Date of Patent: Apr. 10, 2012

(54) HERBAL MEDICINE FOR OSTEOPOROSIS AND RELATED CONDITIONS

(75) Inventors: San-Bao Hwang, Singapore (SG); Priya Gupta, Singapore (SG); Shiau Chuen Cheah, Singapore (SG)

(73) Assignee: Medipearl Pte Ltd., Singapore (SG)

( * ) Notice: Subject to any disclaimer, the term of this patent is extended or adjusted under 35 U.S.C. 154(b) by 162 days.

(21) Appl. No.: 12/273,811

(22) Filed: Nov. 19, 2008

(65) Prior Publication Data
US 2009/0186102 A1  Jul. 23, 2009

(30) Foreign Application Priority Data
Nov. 20, 2007 (GB) .................................. 0722758.0

(51) Int. Cl.
*A61K 36/00* (2006.01)
(52) U.S. Cl. ....................................................... 424/725
(58) Field of Classification Search .................... None
See application file for complete search history.

(56) References Cited

U.S. PATENT DOCUMENTS
2004/0191344 A1* 9/2004 Wang et al. .................. 424/776

FOREIGN PATENT DOCUMENTS

| | | | |
|---|---|---|---|
| CN | 1096204 A | * | 12/1994 |
| CN | 1368375 A | * | 11/2002 |
| CN | 101069716 A | * | 11/2007 |
| JP | 04169536 A | * | 6/1992 |
| KR | 373497 B | * | 2/2003 |

OTHER PUBLICATIONS

Cannell, Richard, Ed., Natural Products Isolation; 1998, Humana Press, Totowa, New Jersey: pp. 40, 40(b), 41, 141, 144, 146, 146(b).*

* cited by examiner

*Primary Examiner* — Patricia Leith
(74) *Attorney, Agent, or Firm* — B. Aaron Schulman, Esq.; Terry L. Wright, Esq.; Stites & Harbison PLLC (57) ABSTRACT

A composition derived from six plant materials: ((i) Herba epimedii (Yin Yang Huo) (ii) Fructus Psoraleae (*Psoralea coryfolia*) (Bu Gu Zhi) (iii) Radix Rehmanniae preparatae (*Rehmannia glutinosa*) (Shu Di) (iv) Cortex Eucommiae (Du Zhong) (v) Fructus Cnidii (She Chuang Zhi) (vi) Radix Astragali (*Astragalus Membranaceus*) (Huang Qi)) is useful in treating conditions linked to the activity of osteoblasts and/or osteoclasts, such as osteoporosis and other conditions relating to bone mass or the menopause; obesity; glucose intolerance; and diabetes.

9 Claims, 7 Drawing Sheets

FIG. 1(iii)

FIG. 3(iii)

HERBAL MEDICINE FOR OSTEOPOROSIS AND RELATED CONDITIONS

BACKGROUND OF THE INVENTION

The present invention relates to a herbal medicine useful for the treatment of osteoporosis and other conditions. It may be of use in the prevention or treatment of obesity and diabetes. The medicine is derived from a number of plant materials used in traditional Chinese medicine. More specifically, we have found that a mixture of six herbal materials has desirable activities. Furthermore, the activities of the mixture may be enhanced by fractionation/purification. Desirably the individual herbal materials are fractionated/purified in individually appropriate ways prior to mixing with the other materials.

Osteoporosis is a disease of the skeleton in which the bone loses density. Bones become brittle and prone to fracture. Osteoporosis is diagnosed when bone density has decreased to the point where fractures will happen with mild stress. Bones most likely to break from osteoporosis are in the hip, wrist, and spine. Women past menopause are the group most likely to develop osteoporosis, but it is not uncommon in men over 65.

Bone remodelling is the process in which bones are broken down through resorption and then built back up again through bone formation. This is a natural process that takes place all the time on different parts of skeletal bone. Usually these two processes balance each other out and a stable level of bone mass is maintained. Until a healthy person is around 40, the process of breaking down and building up bone by cells called osteoclasts and osteoblasts is a nearly perfectly coupled system, with one phase stimulating the other. As a person ages, however, or in the presence of certain conditions, this system breaks down and the two processes become unbalanced.

Osteoclasts are specialized bone cells that break down bone mass through a process often called resorption of bone. The action of osteoclasts is balanced by the activity of osteoblasts that build up bone mass. In the bones of healthy adults, bone mass remains relatively stable because osteoblasts and osteoclasts are balancing each other and working together to maintain the bone mass. This allows bones to continuously remodel and to heal when damaged. The function of osteoclasts can be affected by various drugs and key nutrients.

In a recent publication, Lee and colleagues (2007) make the surprising observation that bone, a tissue not previously thought to impact bioenergetics, can affect adiposity, glucose metabolism, and insulin sensitivity. People with obesity and diabetes are known to have abnormalities of bone metabolism. Increased adiposity is a risk factor for fracture in children, and diabetics are prone to fracture, although there is little evidence that they are predisposed to osteoporosis (Schwartz et al., 2001).

However, the rate of bone turnover is decreased in diabetics as reflected by diminished expression of biomarkers of bone resorption and formation, including osteocalcin, an osteoblast specific protein (Gerdhem et al., 2005, Osteoporosis Int., 16, (506-1512). Common thinking holds that the decrease in osteoblast activity (the cells that build bone) results from the consequences of diabetes including hyperglycemia, and decreased levels or effectiveness of insulin and IGF-1 (Inaba, 2004). Lee et al. (2007) now present data to challenge this notion and raise the provocative concept that the reduction in osteoblast function may contribute to obesity and glucose intolerance. In this scenario, a vicious cycle would exist in which the metabolic sequelae of diabetes suppress osteoblast function, leading to diminished osteocalcin bioactivity, which in turn further aggravates obesity and insulin resistance.

SUMMARY OF THE INVENTION

We have developed a medicine that can alleviate or prevent (or at least delay the onset of) osteoporosis and related conditions by a double-pronged attack, in that it can both increase the bone-building activity (due to osteoblasts) and decrease the bone resorption activity (due to osteoclasts). Thus the medicine can be used for one or more of the following:
1. Treating osteoporosis
2. Reducing rate of bone fractures
3. Increasing bone mineral density
4. Restoring bone structure
5. Alleviation of menopausal symptoms such as dryness and hot flushes Furthermore the medicine may be used in the treatment of other conditions linked to the activities of osteoblasts and/or osteoclasts. These may include obesity, glucose intolerance and/or diabetes.

Our medicine has been demonstrated to promote the proliferation of osteoblasts. Therefore, it is expected to reduce the body weight through the activation mechanism of osteoblasts.

In further aspects the invention relates to methods of treatment of mammals (human and non-human); methods of manufacturing medicines (which may comprise steps of fractionating components); and use of herbal components in the manufacture of compositions for use in therapy.

The present invention relates to a composition derived from six plant materials:
(i) Herba epimedii (Yin Yang Huo)
(ii) Fructus Psoraleae (*Psoralea coryfolia*) (Bu Gu Zhi)
(iii) Radix Rehmanniae preparatae (*Rehmannia glutinosa*) (Shu Di)
(iv) Cortex Eucommiae (Du Zhong)
(v) Fructus Cnidii (She Chuang Zhi)
(vi) Radix Astragali (*Astragalus Membranaceus*) (Huang Qi)

Some components of these plant materials have been reported in the literature. For example, geniposidic acid from Du Zhong (Kim et al 2003), osthole from She Chuang Zi (Kuo et al. 2005), corylin and bavachin from Bu Gu Zhi (Wang et al. 2001) (Xiong et al, 2003), icarrin from Yin Yang Huo (Xie et al. 2005) and polysaccharides from Shu Di (Oha et al. 2003) and Huang Qi were reported.

Preferred compositions of the invention contain extracts of the 6 herbal materials in the ratio (in parts by weight):
(iv) Du Zhong: 2.5-10, preferably 4-8, most preferably 5 parts
(ii) Bu Gu Zi: 1.5-6, preferably 2-4, most preferably 3 parts
(iii) Shu Di: 1.2-5.0, preferably 1.5-3, most preferably 2.5 parts
(v) She Chuang Zhi: 1-4, preferably 1.2-2.8, most preferably 2 parts
(vi) Huang Qi: 0.3-1.5, preferably 0.5-1.0, most preferably 0.75 parts
(i) Yin Yang Huo: 0.15-0.75, preferably 0.25-0.5, most preferably 0.375 parts The extracts are preferably produced by ethanol extraction for (i), (ii), (iv) and (v), and water-extraction for (iii) and (vi). These initial extracts may be partially purified, suitable techniques being illustrated herein.

Compositions of the invention may contain further components, e.g. conventional adjuvants and/or excipients. They may contain further active ingredients, e.g. a source of calcium such as calcium carbonate which may be provided by oyster shell or pearl powder. Suitably the composition, which may be in a unit dosage form, provides 0-1400 mg of calcium daily.

Excipients may include lactose or starch. Other common excipients include magnesium stearate, dextrin, povidone, celluloses, talc and sucrose. One function may be to counteract a tendency of the herbal materials to absorb moisture and become lumpy. Other possible functions of excipients include flavouring (e.g. sweeteners) and colouring. Excipients may comprise binders, distintegrants, fillers (diluents) and lubricants. Liquid formulations may include liquid vehicles, e.g. water.

DESCRIPTION OF THE PREFERRED EMBODIMENTS

Extraction Procedures

We extracted the six herbs, individually, with 70% aqueous ethanol and with water, and compared the results. For each herb, 3 different samples from different sources were used.

(a) Extraction of Raw Herb (i) (Yin Yang Huo):
(a) using 70% EtOH: 500 g of dried leaves of Ying Yang Huo were ground and extracted with 4 L of 70% EtOH (ACS grade ethanol obtained from Megachem) for one hour, three times, under reflux. The combined extract was filtered and the filtrate was concentrated and dried under vacuum.
(b) using water: 500 g of dried leaves of Yin Yang Huo were ground and extracted with 5 L of water for two hours, two times, under reflux. The combined extract was filtered and the filtrate was concentrated and dried under vacuum.

(b) Extraction of Raw Herb (ii) (Bu Gu Zhi):
(a) using 70% EtOH: 500 g of dried fruit of Bu Gu Zhi was ground and extracted with 4 L of 70% EtOH for one hour, three times, under reflux. The combined extract was filtered and the filtrate was concentrated and dried under vacuum.
(b) using water: 500 g of dried fruit of Bu Gu Zhi was grinded and extracted with 5 L of water for two hours, two times, under reflux. The combined extract was filtered and the filtrate was concentrated and dried under vacuum.

(c) Extraction of Raw Herb (iii) (Shu Di):
(a) using 70% EtOH: Dried herb of Shu Di (500 g) was extracted with 4 L of 70% EtOH for one hour, three times, under reflux. The extracts were filtered and the filtrate was concentrated and dried under vacuum.
(b) using water: Dried herb of Shu Di (500 g) was extracted with 5 L of water for two hours, two times, under reflux. The extracts were filtered and the filtrate was concentrated and dried under vacuum.

(d) Extraction of Raw Herb (iv) (Du Zhong):
(a) using 70% EtOH: Air dried bark of Du Zhong (500 g) was chopped and extracted with 4 L of 70% EtOH for one hour, three times, under reflux. The combined extract was filtered and the filtrate was concentrated and dried under vacuum.
(b) using water: 500 g of dried bark of Du Zhong was chopped and extracted with 5 L of water for two hours, two times, under reflux. The combined extract was filtered and the filtrate was concentrated and dried under vacuum.

(e) Extraction of Raw Herb (v) (She Chuang Zhi):
(a) using 70% EtOH: 500 g of dried fruit of She Chuang Zhi was chopped and extracted with 4 L of 70% EtOH for one hour, three times, under reflux. The combined extract was filtered and the filtrate was concentrated and dried under vacuum.
(b) using water: 500 g of dried fruit of She Chuang Zhi was chopped and extracted with 5 L of water for two hours, two times, under reflux. The combined extract was filtered and the filtrate was concentrated and dried under vacuum.

(f) Extraction of Raw Herb (vi) (Huang Qi):
(a) using 70% EtOH: 500 g of dried root of Huang Qi was extracted with 4 L of 70% EtOH for one hour, three times, under reflux. The combined extract was filtered and the filtrate was concentrated and dried under vacuum.
(b) using water: 500 g of dried root of Huang Qi was extracted with 5 L of water for two hours, two times, under reflux. The combined extract was filtered and the filtrate was concentrated and dried under vacuum.

HPLC Analysis of the Crude Extracts:

HPLC analyses of the extracts were carried out using a Waters 2695 separation module coupled with Waters 2487 Dual λ Absorbance Detector and Empower Pro software. The HPLC system was equipped with a C18 Column (250×4.6 mm, 5 µm), C18 Guard Cartridge, 3 mm. The analyses were performed at room temperature. Each sample was prepared at 1 mg/ml concentration using 60% EtOH as solvent. The injection volume of the sample was 20 µl. The mobile phase was a mixture of acetonitrile and 0.1% formic acid at a flow rate of 1.0 ml/min and method used was fullscan_2b. HPLC chromatograms were recorded at 254 nm and 315 nm of wavelength. Details of the HPLC method are shown in Table 1.

TABLE 1

| HPLC method | | |
|---|---|---|
| 1% formic acid in $H_2O$ % | ACN % | Time (min) |
| 96 | 5 | 0 |
| 50 | 50 | 30 |

TABLE 1-continued

| HPLC method | | |
|---|---|---|
| 1% formic acid in H$_2$O % | ACN % | Time (min) |
| 20 | 80 | 31 |
| 20 | 80 | 34 |
| 96 | 4 | 35 |
| 96 | 4 | 40 |

HPLC grade solvents were purchased from Fisher Scientific and Standard samples Osthole and Icarrin were purchased from China Pharmaceutical and Biological manufacturer and the standard Geniposidic acid was obtained from Chroma Dex.

Results of the HPLC analysis are included in Table 2.

TABLE 2

Extraction Yields and Active Components from Three Different Sources of China

| | Extraction Yield | | Active component % | |
|---|---|---|---|---|
| Raw Herb | Water | 70% EtOH | Water Extraction | 70% EtOH extraction |
| Bu Gu Zhi (ii) | 28.55% | 30% | — | — |
| | 39.33% | 29.16% | — | — |
| | 31.09% | 27.90% | — | — |
| She Chuang Zhi (v) | 20.07% | 21% | No peak | 0.91% (Osthole) |
| | 24.68% | 18.48% | No peak | 1.56% (Osthole) |
| | 16.86% | 22.47% | No peak | 1.90% (Osthole) |
| Du Zhong (iv) | 14% | 15% | 0.12% (GPA) | 0.27% (GPA) |
| | 14.03% | 12.14% | 0.90% (GPA) | 2.33% (GPA) |
| | 12.80% | 15.63% | 0.17% (GPA) | 1.22% (GPA) |
| Yin Yang Huo (i) | 22% | 17.30% | 0.28% (Icarrin) | 0.75% (Icarrin) |
| | 11.53% | 11.62% | 0.25% (Icarrin) | 2.86% (Icarrin) |
| | 15.72% | 12.95% | 0.59% (Icarrin) | 0.85% (Icarrin) |
| Shu Di (iii) | 76% | 67.65% | — | — |
| | 68.10% | 61.87% | — | — |
| | 70.31% | 65.61% | — | — |
| Huang Qi (vi) | 54% | 34% | — | — |
| | 36.35% | 29.40% | — | — |
| | 36.20% | 33.24% | — | — |

From the results, it was concluded to use extraction with 70%.EtOH for herbs (i), (ii), (iv) and (v); and extraction with water for herbs (iii) and (vi).

Preparation of Extracts (Larger Scale):
Extraction:

Extraction of raw herb (i) (Yin Yang Huo) using 70% EtOH: 2 kg of dried leaves of Ying Yang Huo were ground and extracted with 16 L of 70% EtOH for one hour, three times, under reflux. The combined extract was filtered and the filtrate was concentrated and dried under vacuum.
Yield: 12.98%

Extraction of raw herb (ii) (Bu Gu Zhi) using 70% EtOH: 750 g of dried fruit of Bu Gu Zhi (obtained from He Bei) was ground and extracted with 6 L of 70% EtOH for one hour, three times, under reflux. The combined extract was filtered and the filtrate was concentrated and dried under vacuum.
Yield: 29.3%

Extraction of raw herb (iv) (Du Zhong) using 70% EtOH: Air Dried bark of Du Zhong (1.5 kg) was chopped and extracted with 12 L of 70% EtOH for one hour, three times, under reflux. The combined extract was filtered and the filtrate was concentrated and dried under vacuum.
Yield: 12.14%

Extraction of raw herb (v) (She Chuang Zhi) using 70% EtOH: 700 g of dried fruit of She Chuang Zhi was chopped and extracted with 5.6 L of 70% EtOH for one hour, three times, under reflux. The combined extract was filtered and the filtrate was concentrated and dried under vacuum.
Yield: 22.74%

Extraction of raw herb of (iii) (Shu Di) using water: Dried herb of Shu Di (300 g) was extracted with 3 L of water for two hours, two times, under reflux. The combined extract was filtered and the filtrate was concentrated and dried under vacuum.
Yield: 55.8%

Extraction of raw herb (vi) (Huang Qi) using water: 600 g of dried root of Huang Qi was extracted with 6 L of water for two hours, two times, under reflux. The combined extract was filtered and the filtrate was concentrated and dried in vacuum.
Yield: 29.8%

Preparation of Composition (Unrefined)

The extracts of the raw herbs obtained above, were mixed in the ratio (Bu Gu Zhi:She Chuang Zi:Yin Yang Huo:Shu Di:Du Zhong:Huang Qi 1.5:1:1.5:1.25:1.25:1.5) to get 1 kg of the composition.

| Name of herb | Quantity of crude extract |
|---|---|
| Bu Gu Zhi (ii) | 187.5 g |
| She Chuang Zi (v) | 125 g |
| Yin Yang Huo (i) | 187.5 g |
| Shu Di (iii) | 156.25 g |
| Du Zhong (iv) | 156.25 g |
| Huang Qi (vi) | 187.5 g |

Procedures for Partial Purification (or "Fractionation") of the Extracts were Developed:

Partial purification of crude extract of (i) (Yin Yang Huo): a column (55×700 mm) was packed with Silica gel (60-230 mesh) using ethyl acetate. A slurry of 35 g of the crude extract (70% EtOH extract) of Yin Yang Huo was prepared using 350 g of Silica gel in MeOH. Active fraction was eluted using 20% MeOH in ethyl acetate (5 litres) as eluant. Fraction was concentrated and dried in vacuum. Same procedure repeated for 10 times.
Yield: 29.4%

Partial purification of crude extract of (ii) (Bu Gu Zhi): we used a lipophilic crosslinked dextran-based resin (in this example, Sephadex LH-20) This was pre-swelled in MeOH overnight and then packed in a Column (55×700 mm). 3 5 g of the crude extract (70% EtOH extract) of Bu Gu Zhi was dissolved in 100 ml of MeOH using sonication and loaded onto the column. Approximately 4 litres of MeOH was used as eluant. MeOH fraction was concentrated and evaporated to dryness under vacuum. The same procedure was repeated 4 times.
Yield: 70.1%

Partial purification of crude extract of (iii) (Shu Di): 358 g of the crude extract (water extract) of Shu Di was taken and dissolved in 350 ml of water, and then 100% EtOH was added slowly in order to form a precipitate. The total amount of 100% EtOH added was 2.8 L. The mixture was kept in a refrigerator overnight for complete precipitation, then filtered. The residue obtained was vacuum dried for 24 hours.
Yield: 29.32%

Partial purification of crude extract of (iv) (Du Zhong): a column (55×700 mm) was packed with Silica gel (60-230 mesh) using acetone. A slurry of 35 g of the crude extract (70% EtOH extract) of Du Zhong was prepared using 350 g of Silica gel in MeOH. Active fraction was eluted using acetone (10 litres) as eluant. Fraction was concentrated and dried under vacuum. Same procedure repeated for 6 times.
Yield: 29.4%

Partial purification of crude extract of (v) (She Chuang Zhi): 200 g of the crude extract (70% EtOH extract) of She Chuang Zhi was placed in a 5 L round bottom flask. Acetone (4l) was added and stirred for 1 hour, then filtered. The residue was stirred for 1 hour with a further 4l of acetone. The procedure was repeated 6 times. Finally all the eight filtrates were combined and concentrated and dried overnight under vacuum.
Yield: 41.41%

Partial purification of crude extract of (iv) (Huang Qi): 158 g of the crude extract (water extract) of Huang Qi was taken and dissolved in 150 ml of water, then 100% EtOH was added slowly in order to form a precipitate. The total amount of 100% EtOH added was 1.2 L. The mixture was kept in a refrigerator overnight for complete precipitation, then filtered. The residue obtained was vacuum dried for 24 hours.
Yield: 64.5%

The partially purified or fractionated samples of the crude extracts of the raw herbs obtained above were mixed in the ratio (Bu Gu Zhi:She Chuang Zi:Yin Yang Huo:Shu Di:Du Zhong Huang Qi 1.5:1:1.5:1.25:1.25:1.5) to get 500 g of GMA partial purified sample.

| Name of herb | Quantity of partially purified samples |
| --- | --- |
| Bu Gu Zhi | 93.75 g |
| She Chuang Zi | 62.5 g |
| Yin Yang Huo | 93.75 g |
| Shu Di | 78.125 g |
| Du Zhong | 78.125 g |
| Huang Qi | 93.75 g |

Action of Crude and Partially Purified Herb Extracts on Osteoclasts

A study was made to elucidate the effectiveness of the herbs on anti-proliferation of rat osteoclast cells in vitro.
Materials All media components were purchased from Sigma-Aldrich (USA) unless otherwise stated. Fetus bovine serum was purchased from Hyclone, USA. TRAP staining kit, 0.25% Trysin-EDTA solution, MTT (Thiazolyl Blue Tetrazolium Bromide) and DMSO were purchased from Sigma-Aldrich, USA. All chemicals were the highest grade available from Sigma Chemical Co. 96-wells plates were bought from NUNC, Denmark.
Methods
Preparation of Osteoclast Cultures Femurs were obtained, from 3-4 weeks old young female wistar rats (100-125 g), following sacrifice. Femurs were washed through 4 washes (30 ml each time) with femur wash medium, α-minimum essential medium (α-MEM) containing 1 mg/ml Penicillin G, 0.5 mg/ml gentamycin and 3 mg/ml fungizone. Epiphyses were removed from rat femurs. Bone marrow cells were obtained by using a syringe for flushing femurs from both ends of the shaft with α-MEM containing 15% (v/v) fetal bovine serum (Hyclone), 0.1 mg/ml penicillin G, 0.05 mg/ml gentamycin, 300 ng/ml fungizone, 0.28 mM L-Ascorbic Acid 2-Phosphate, 10 nM dexamethasone, 10 ng/ml M-CSF, 10 ng/ml RANKL and 10 ng/ml TNF-α. Medium was collected from both end of femurs and centrifuged at 300 g for 3 minutes. After centrifugation, two thirds of the supernatant from the top was removed. The remaining fractions were used as a source of osteoclast precursors. Cell suspensions were mixed and inoculates 0.1 ml ($1 \times 10^5$ bone marrow cells) onto each well in 96 wells-plate (NUNC). The cells were incubated in 37° C., 5% $CO_2$, 100% humidity. Medium was changed after 24 hours with osteoclast medium and cells were refeed 3 times weekly.
TRAP-Positive Cell Staining Osteoclast cells were suspended in phenol α-MEM containing 15% FBS and plated at a concentration of $5 \times 10^5$ cells/well into a 24-well culture dish in the presence of 10 ng/ml RANKL and incubated for 24 h. The medium and factors were replaced after 3 days. After 5 days of culture, the cells were fixed and stained for tartrate-resistant acid phosphatase (TRAP), a typical marker enzyme of osteoclast using the commercial TRAP staining kit (Sigma, 387-A) according to the manufacturer's instructions. TRAP+ cells with more than three nuclei were counted as TRAP positive MNCs.
Proliferation Assay Dose-response curves for the crude and partially purified extracts, individually and as the combination of 6 herbs, were determined by the anti-proliferation assay determined by MTT (Thiazolyl Blue Tetrazolium Bromide) on the percent survival of the rat osteoclast cells on a 96-well microtitre plate. 10,000 viable cancer cells at exponential growth phase in 100 μl were seeded into each well of a 96-well microtitre plate. The cells were cultured overnight for cell attachment at 37° C. in 5% carbon dioxide atmosphere. The used medium from each well was discarded the next morning and 200 μl of fresh media were added. 2 μl of herb samples at various concentrations were added into each well and the plate was incubated at 37° C. in 5% carbon dioxide atmosphere for 24 hours.

The appropriate amount of MTT was dissolved in serum-free medium to obtain a concentration of 1 mg/ml medium. 50 μl of the MTT solution was transferred into each well. Cells were incubated for 4 hrs at 37° C. in 5% carbon dioxide atmosphere. Medium was aspirated from the well and 150 μl DMSO was added into each well to dissolve the blue formazan precipitate. Optical absorbance of the reduced MTT was then measured at 550 nm using a microtiter plate reader. The percent viable cells were calculated with the following: Sample OD/Control OD×100%.
Results FIG. 1 contains graphs showing the anti-proliferation activity of the various materials on osteoclasts. All values are expressed as mean±standard deviation.

Triangles relate to crude extracts; squares relate to partially purified materials.

FIG. 1 (i) shows that the crude extract of Yin Yang Huo inhibited the proliferation of osteoclast cells (37%) at 500 μg/ml, whereas the partially purified fraction that contained icarrin inhibited 54% of osteoclast cells proliferation at 500 μg/ml. Yin Yang Huo modulated osteoclastogenesis by inhibiting the proliferation of osteoclast cells (Xie et al. 2005). Besides that, Yin Yang Huo treatment can effectively suppress the OVX-induced increase in bone turnover possibly by both an increase in osteoblastic activities and a decrease in osteoclastogenesis (Xie et al. 2005).

Figure 1:
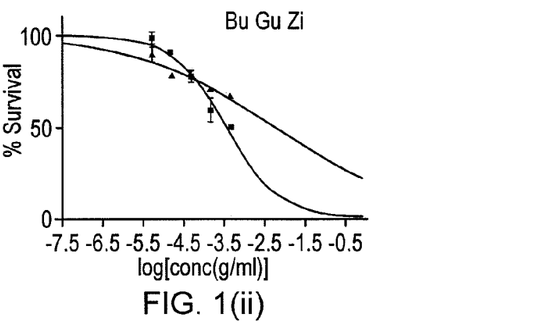
Figure 1I:
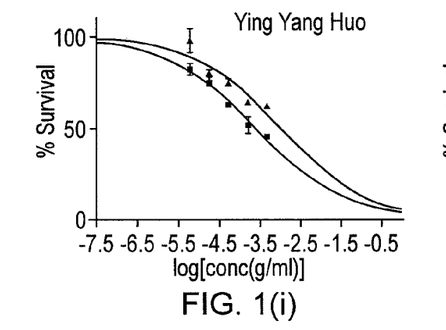
FIG. 1(i) to (vi) is a set of graphs illustrating the activity of 6 individual herbal extracts on osteoclasts.

FIG. 1 (ii) shows that the crude extract of Bu Gu Zhi inhibited proliferation (33%) of osteoclast cells at 500 μg/ml. But the partial purified fraction that contained corylin and bavachin inhibited the proliferation of osteoclast cells effectively (50%) at 500 μg/ml. Concentration that needed to inhibited the proliferation of osteoclast cells is lesser in the partial purified fraction compare with the crude extract of Bu Gu Zhi.

FIG. 1 (iii) shows that crude extract of Shu Di inhibited the proliferation of osteoclast (37%) cells at 500 μg/ml. The partially purified fraction from Shu Di that contained polysaccharides inhibited 48% of the proliferation of osteoclast cells, which was 11% more compared with the crude extract. Du Zhong, Shu Di inhibited the proliferation of osteoclast cells in a dose-dependent manner.

FIG. 1 (*iv*) shows that Du Zhong inhibited the proliferation of osteoclast cells in a dose-dependent manner. Crude extract of Du Zhong inhibited the proliferation (30%) of osteoclast cells at 500 µg/ml, whereas partial purified fraction from crude extract that contained geniposidic acid (GPA) inhibited effectively the proliferation as 47% of osteoclast cells at 500 µg/ml.

Figure 1V:
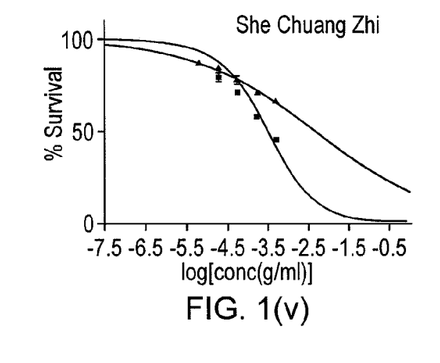

FIG. 1 (*v*) shows that crude extract of She Chuang Zhi inhibited proliferation of osteoclast cells at 500 µg/ml (32%). Partially purified fraction that contained osthole inhibited proliferation of osteoclast cells at 500 µg/ml as much as 54%. She Chuang Zhi inhibited osteoclast formation and differentiation also reported by Qin et al. 2003. She Chuang Zi inhibited osteoclast formation and differentiation by decreased and inhibited TRAP activity of osteoclasts. Besides that, it also decreased the osteoclastic bone resorption pit area and $Ca^{2+}$ release from bone slices (Qin et al. 2003).

FIG. 1 (*vi*) shows that crude extract of Huang Qi inhibited the proliferation of osteoclast cells at 500 µg/ml (31%). The partially purified fraction that contained polysaccharides showed the enhancement of the anti-proliferation effects on osteoclast cells at 50 µg/ml (48%). Concentration needed to inhibit the osteoclast cells is lesser in the partial purified compared with the crude extract of Huang Qi.

For all the 6 herbs, the partially purified fraction showed greater positive results compared with the crude extract. The anti-proliferation effects on osteoclast cells are summarized in Table 3.

Potency of the fractionated components can also be expressed as $ED_{50}$ (the concentration of crude extracted or partially fractionated component to have 50% inhibition). The results are summarized in Table 4.

TABLE 3

Summary of the anti-proliferation activity on osteoclast cells of individual herb extracts before and after partial purification.

| Name | Origin | Activity of crude extract at 500 µg/ml on osteoclast cells | Active component | Activity of active fraction at 500 µg/ml on osteoclast cells |
|---|---|---|---|---|
| Shu Di | He Bei | Inhibited 37% proliferation | Polysaccharide | Inhibited 48% proliferation |
| Huang Qi | He Bei | Inhibited 31% proliferation | Polysaccharide | Inhibited 48% proliferation |
| She Chuang Zi | He Bei | Inhibited 33% proliferation | Osthole | Inhibited 54% proliferation |
| Yin Yang Huo | Shi Chuan | Inhibited 37% proliferation | Icarrin | Inhibited 54% proliferation |
| Du Zhong | Bo Chou | Inhibited 30% proliferation | GPA | Inhibited 47% proliferation |
| Bu Gu Zhi | He Bei | Inhibited 33% proliferation | Corylin & Bavachin | Inhibited 50% proliferation |

TABLE 4

$ED_{50}$ of the anti-proliferation activity on osteoclast cells of individual herb extracts before and after partial purification.

| | | $EC_{50}$ (g/ml) | Rel Potency |
|---|---|---|---|
| Shu Di | Partially purified | 4.83E−04 | 4.22 |
| | Crude Extract | 2.04E−03 | |
| Huang Qi | Partially purified | 4.53E−04 | 14.97 |
| | Crude Extract | 6.78E−03 | |
| She Chuang Zi | Partially purified | 3.03E−04 | 15.63 |
| | Crude Extract | 4.73E−03 | |
| Du Zhong | Partially purified | 4.95E−04 | 5.85 |
| | Crude Extract | 2.90E−03 | |
| Bu Gu Zhi | Partially purified | 4.06E−04 | 15.92 |
| | Crude Extract | 6.46E−03 | |
| Ying Yang Huo | Partially purified | 2.70E−04 | 4.38 |
| | Crude Extract | 1.18E−03 | |

Similar tests were carried out using compositions of 6 crude extracts (2 versions) and 6 partially purified extracts. The results are displayed in FIG. 2, where solid circles represent the first crude composition; triangles represent the second crude composition; and open circles represent the partially purified composition.

Figure 2:
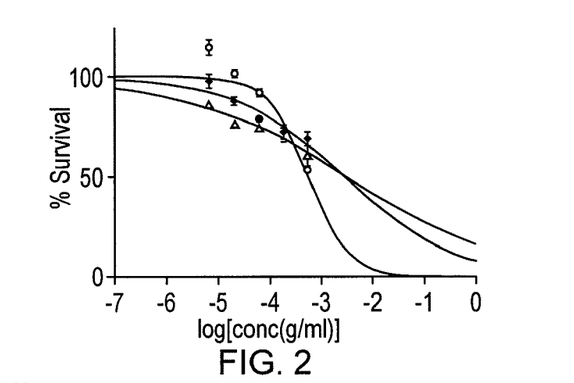
FIG. 2 is a graph like those of FIG. 1 but illustrating the activity of mixtures of extracts of all 6 herbal materials.

The second version of the crude extract gave a better activity in inhibiting proliferation of osteoclast cells compared with the first version at the same concentration. Moreover, the partially purified fraction (which was derived from the extracts used in the second crude extract) inhibited 46% growth of osteoclast cells at 500 µg/ml compared with the second version of the crude extract which inhibited 39% growth at 500 µg/ml.

| The $EC_{50}$ values were: | |
|---|---|
| 1$^{st}$ crude | $2.71 \times 10^{-3}$ g/ml |
| 2$^{nd}$ crude | $2.94 \times 10^{-3}$ g/ml |
| Partially purified | $5.27 \times 10^{-4}$ g/ml |

Action of Crude and Partially Purified Herb Extracts on Osteoblasts

A study was made to elucidate the effectiveness of the herbs on the proliferation of hFOB human osteoblast cells.

Materials

The conditionally immortalized human fetal osteoblastic cell line hFOB was obtained from the American Type Culture Collection (ATCC) (Manassas, Va., http://www.atcc.org). hFOB was developed by conditionally immortalizing human fetal osteoblasts with a temperature-sensitive mutant of the SV40 large T antigen (ts-SV40LTA) gene. At the permissive temperature of 33.5° C., the ts-SV40LTA is active and the hFOB cells proliferate rapidly, whereas at the nonpermissive temperature of 39.5° C., the ts-SV40LTA is inactive, and the cells differentiate and display the phenotype of mature osteoblasts. Fetus bovine serum was purchased Hyclone, USA. G418, Ham's 12:DMEM (1:1), 0.25% Trypsin-EDTA solution, MTT (Thiazolyl Blue Tetrazolium Bromide) and DMSO were purchased from Sigma-Aldrich, USA. 96-well plate was bought from NUNC, Denmark.

Methods

Cell Lines

The hFOB cells were cultured according to ATCC protocol in a 1:1 mixture of Ham's F12 medium and Dulbecco's modified Eagle's medium (DMEM) supplemented with 10% fetal bovine serum, 0.3 mg/ml G418, hereafter called complete medium. Cells were cultured at 34° C. in a humidified atmosphere of 5% $CO_2$/95% air.

Proliferation Assay

Dose-response curves of the six individual herb crude extracts, the six partially purified fractions, and compositions containing material from all six herbs were determined by proliferation assay determined by MTT (Thiazolyl Blue Tetrazolium Bromide) on the percent survival of the osteoblast cells, hFOB on a 96-well microtitre plate.

10,000 viable cancer cells at exponential growth phase in 100 μl were seeded into each well of a 96-well microtitre plate. The cells were cultured overnight for cell attachment at 37° C. in 5% carbon dioxide atmosphere. The used medium from each well was discarded in the next morning and 200 μl of fresh media were added. 2 μl of herbal samples at various concentrations were added into each well and the plate was incubated at 37° C. in 5% carbon dioxide atmosphere for 24 hours.

MTT was dissolved in serum-free medium to obtain a concentration of 1 mg MTT/ml medium. 50 μl of MTT solution was transferred into each well. Cells were incubated for 4 hrs at 37° C. in 5% carbon dioxide atmosphere. Medium was aspirated from the well and 150 μl DMSO was added into each well to dissolve the blue formazan precipitate. Optical absorbance of the reduced MTT was then measured at 550 nm using a microtiter plate reader. The percent viable cells were calculated with the following: Sample OD/Control OD×100%

Results

Figure 3:
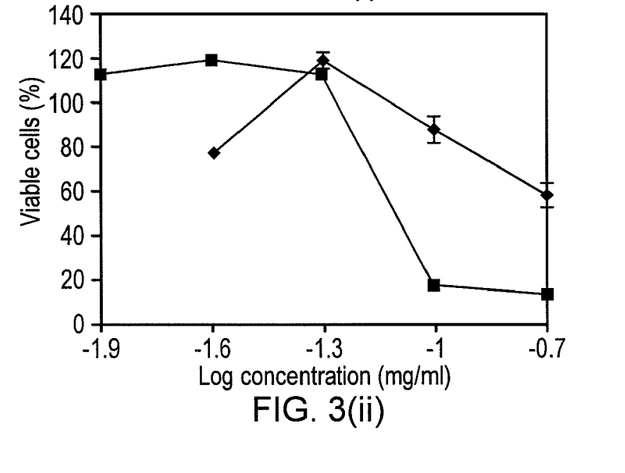

Graphs of the results are shown in FIG. 3. Diamonds represent crude extracts; squares represent partially purified materials. All values are expressed as mean±standard deviation.

Figure 3I:
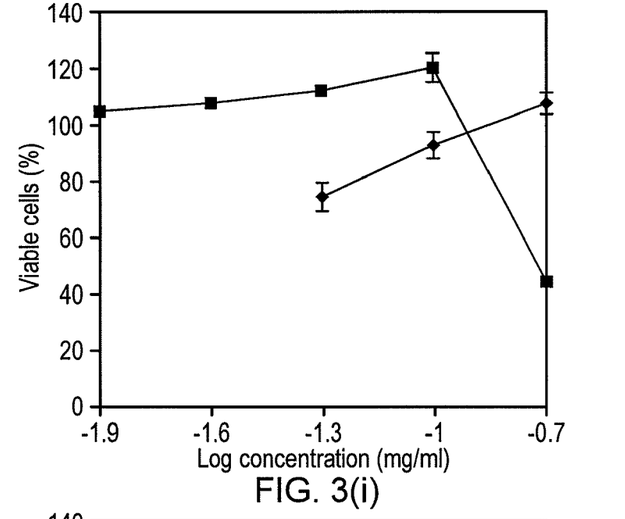
FIG. 3(i) to (vi) is a set of graphs illustrating the activity of 6 individual herbal extracts ((i) Yin Yang Huo; (ii) Bu Gu Zhi; (iii) Shu Di; (iv) Du Zhong; (v) She Chuang Zhi; and (vi) Huang Qi) on osteoblasts.

FIG. 3 (i) shows that crude extract of Yin Yang Huo induced proliferation of hFOB osteoblast cells (8%) at 200 μg/ml, whereas partially purified fraction that contained icarrin induced proliferation of hFOB osteoblast cells (20%) at 100 μg/ml. Concentration needed to induce the osteoblast cells is lesser and the proliferation activity is greater in partially purified fraction compared with the crude extract. Yin Yang Huo increased bone turnover rate to restore the loss of trabecular bone architecture in rats by its direct action of stimulating bone formation and inhibiting bone resorption (Xie et al. 2005).

FIG. 3 (ii) shows that crude extract of Bu Gu Zhi induced proliferation (20%) of hFOB osteoblast cells at 50 μg/ml. But the partially purified fraction that contained corylin and bavachin induced proliferation (20%) of hFOB osteoblast cells at 25 μg/ml. Concentration needed to induce the osteoblast cells is lesser in the partially purified fraction compare with the crude extract of Bu Gu Zhi (50 μg/ml).

Corylin from *Psoralea coryfolia* (Bu Gu Zhi) exhibited osteoblastic proliferation stimulating activity in UMR 106 cell line cultured in vitro. The flavanoids corylin and bavachin were isolated and identified as active principles by activity-guided fractionation (Wang et al. 2001). The results suggested that *Psoralea coryfolia* fruit extracts and corylin and bavachin might stimulate bone formation or have potential activity against osteoporosis. Xiong et al. (2003) also observed the effect of extract and corylin fraction of *Psoralea corylifolia* L. extract on osteoblastic activity. These effects suggest that *Psoralea corylifolia* L. extract and corylin would stimulate bone formation (Xiong et al. 2003).

FIG. 3 (iii) shows that crude extract of Shu Di induced proliferation of hFOB osteoblase (7%) cells at 50 μg/ml. Partially purified fraction from Shu Di that contained polysaccharides did not induce proliferation of hFOB osteoblast cells. There was no improvement in concentration as well as the proliferation activity on osteoblast in partial purified fraction from the crude extract of Shu Di.

FIG. 3 (iv) shows that crude extract of Du Zhong induced little proliferation (5%) of hFOB osteoblast cells at 100 μg/ml, whereas partial purified fraction from crude extract that contained geniposidic acid (GPA) induced more proliferation as 13% of hFOB osteoblast cells at 100 μg/ml.

GPA from Cortex Eucommiae (Du Zhong) increases the proliferation of osteoblast-like cells and augments bone growth and suppresses bone loss also, as reported by Kim et al. (2003). Apart from this, Ha (2003) also reported that the Eucommia bark extract and its constituents, geniposidic acid, geniposide and aucubin increased the proliferation of osteoblast-like cells to stimulate osteogenesis. In addition, using the coculture of mouse bone marrow cells and ST-2 cells, these extracts and compounds inhibited osteoclastic activities (Ha 2003).

Figure 3V:
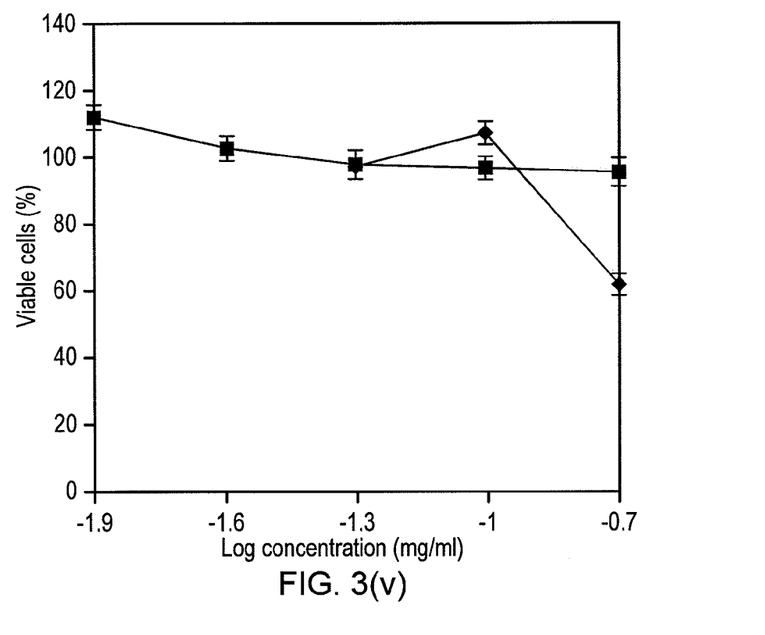

FIG. 3 (v) shows that crude extract of She Chuang Zhi induced proliferation of hFOB osteoblast cells at 100 μg/ml (7%). Partial purified fraction that contained osthole induced proliferation of hFOB osteoblast cells at 12.5 μg/ml (12%). The concentration needed to induce the osteoblast cells is lesser in the partial purified compare with the crude extract of She Chuang Zhi. Kuo et al. (2005) reported that osthole from Fructus Cnidii (She Chuang Zi) significantly induced the differentiation in two human osteoblast-like cell lines, MG-63 and hFOB.

As reported by Meng et al. (2004), extracts from fruits of *Cnidium monnieri* (L.) Cuss (*umbelifera*) were screened using the osteoblast-like UMR106 cells in vitro. Three coumarins (osthole, bergapten and imperatorin) were isolated and their effects on osteoblastic proliferation were investigated. Osthole, a major pharmacologically active constituent, significantly promoted the cells' activity. Bergapten and imperatorin were less effective than osthole. These results suggested *Cnidium monnieri* (L.) Cuss extracts might have potential activity against osteoporosis, and its partial purified fraction might contain active constituents stimulating osteoblasts. (Meng et al. 2004).

As shown in FIG. 3 (vi), crude extract of Huang Qi induced proliferation of hFOB osteoblast cells at 100 μg/ml (17%). The partially purified fraction that contained polysaccharides induced proliferation of hFOB osteoblast cells at 50 μg/ml (15%). The concentration needed to induce the osteoblast cells is lesser in the partially purified compared with the crude extract of Huang Qi.

These results are summarised in Table 5.

TABLE 5 activity of single herb extracts on osteoblasts

| Name | Activity of Crude extract | Active component | Activity of active fraction |
| --- | --- | --- | --- |
| Shu Di | Induced proliferation (10%) at 50 μg/ml | Polysaccharide | No significant improvement |
| Huang Qi | Induced proliferation (17%) at 100 μg/ml | polysaccharide | Induced proliferation (15%) at 50 μg/ml |
| She Chuang Zhi | Induced proliferation (7%) at 100 μg/ml | Osthole | Induced proliferation (12%) at 12.5 μg/ml |
| Yin Yang Huo | Induced proliferation (8%) at 200 μg/ml | Icarrin | Induced proliferation (20%) at 100 μg/ml |
| Du Zhong | Induced proliferation (5%) at 100 μg/ml | GPA | Induced proliferation (13%) at 100 μg/ml |
| Bu Gu Zhi | Induced proliferation (20%) at 50 μg/ml | Corylin & Bavachin | Induced proliferation (20%) at 25 μg/ml |

Figure 4A:
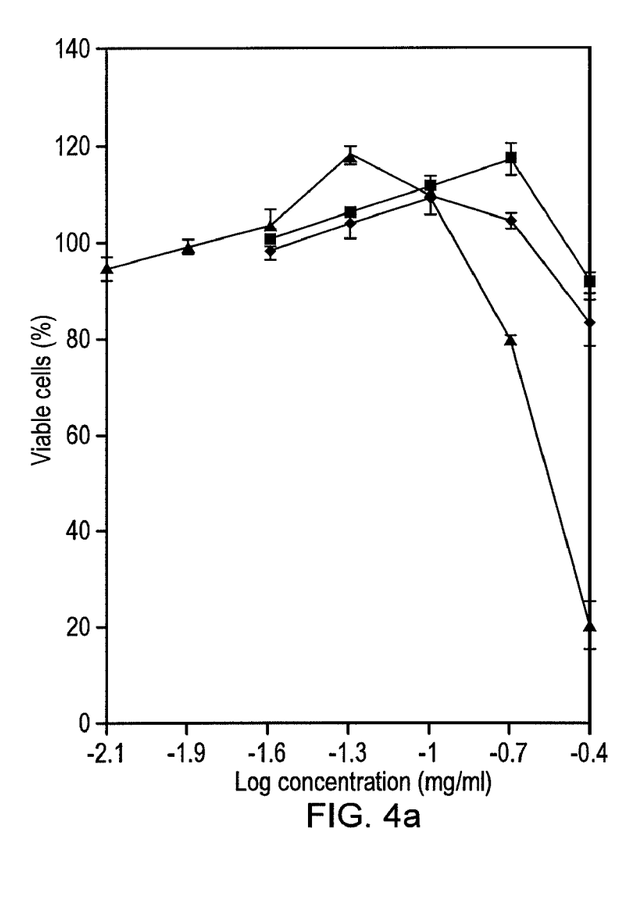
FIG. 4a and FIG. 4b are graphs like those of FIG. 3 but illustrating the activity of mixtures of extracts of all 6 herbal materials, after 24 hrs (FIG. 4a) and 48 hrs (FIG. 4b).
Figure 4B:
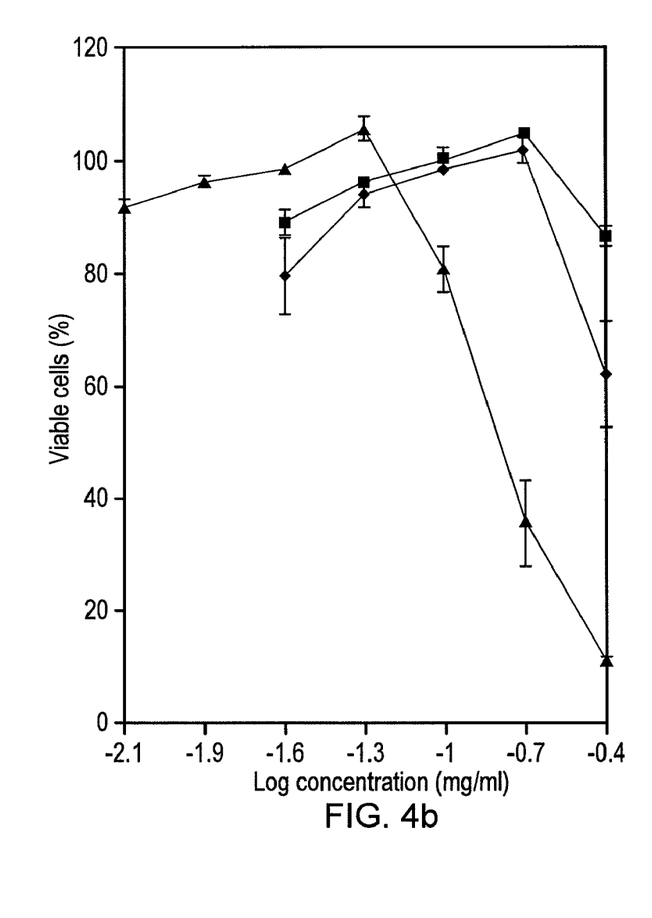

Similar tests were carried out using compositions containing all 6 crude extracts (2 versions) and 6 partially purified extracts. The results are displayed in FIG. 4a (activity after 24 hours) and FIG. 4b (activity after 48 hours). Diamonds and squares represent the first and second versions, respectively, of the "crude" compositions while triangles represent the "purified" compositions. It can be seen that the second version is somewhat more active than the first "crude" version, while the "purified" composition is much more active: after 24 hours (FIG. 4a) the second "crude" version stimulated 17% growth at 200 μg/ml. After 48 hours (FIG. 4b), the proliferation activities on osteoblast cells are not promising after 48 hrs. Only 6% of the proliferation of osteoblast cells can be noted at the 50 μg/ml concentration in 48 hrs partial purified fraction treatment compared with 18% at 50 μg/ml after 24 hrs partial purified fraction treatment. Osteoblast cells (hFOB) died after 48 hrs of treatment with partial purified fraction and crude extract compared to the control cells.

Figure 4C:
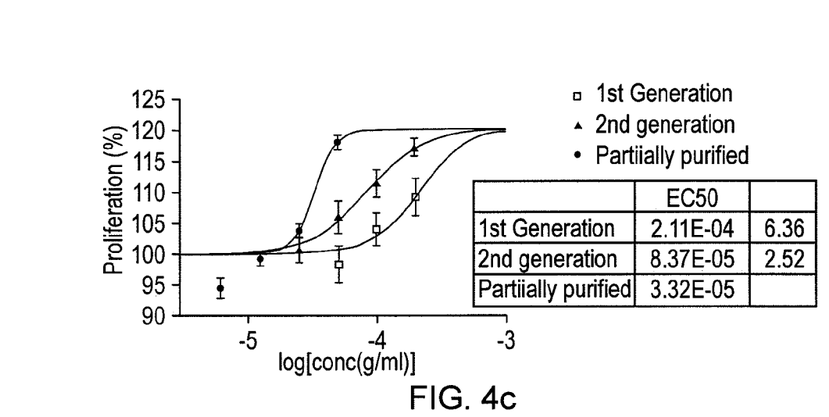
FIG. 4c is a graph showing best fitting curves for activity of the mixtures on proliferation activity of osteoblasts.

The best curve fitting of the first and second "crude" versions and the "purified" composition on the proliferation activity of osteoblasts (hFOB) is shown in FIG. 4c. The squares and triangles represent the first and second "crude" versions while the circles represent the "purified" composition.

Animal Models

Tests have been carried out to measure the effects of the "crude extract" (second "crude" versions) and the "purified" composition.

Materials have been tested in ovariectomized rats, a popular and generally accepted osteoporosis animal model.

After orally dosing continuously for three months at 0.12, 0.25, 0.5 and 0.8 g/kg/day, twice a day, the bone mass index, wet weight and dry weight of femur, bone mineral densities of femur and lumbar were measured and calculated. Body weights of rats were measured weekly. The results are summarized in Tables 6 and 7.

TABLE 6

Bone mass index and wet weight of the femur (mg/cm) from rats of all experimental groups

| Groups | Rat # | Bone Mass Index ($\bar{x} \pm s$) | Wet Weight (mg/cm) ($\bar{x} \pm s$) |
|---|---|---|---|
| Sham-operated Normal Control | 12 | 4.1404 ± 0.36233 | 198.3774 ± 12.47043 |
| Ovariectomized Model | 12 | 3.4909 ± 0.47565## | 190.7690 ± 8.2086 |
| Fosamax ® | 10 | 3.4202 ± 0.24757 | 205.8757 ± 18.31985** |
| Crude Extract | | | |
| 1.4 g/kg | 11 | 3.6026 ± 0.49182 | 193.8621 ± 7.94898 |
| 0.5 g/kg | 10 | 3.4736 ± 0.18521 | 192.6831 ± 13.58409 |
| Partially Purified | | | |
| 0.12 g/Kg | 11 | 3.4200 ± 0.29461 | 188.8743 ± 9.34391 |
| 0.25 g/Kg | 11 | 3.5885 ± 0.24125 | 197.8749 ± 11.43143 |
| 0.5 g/Kg | 11 | 3.7375 ± 0.32996 | 195.5449 ± 23.14863 |
| 0.8 g/Kg | 6 | 4.1492 ± 0.34708** | 197.7648 ± 12.56049 |

Figure 5:
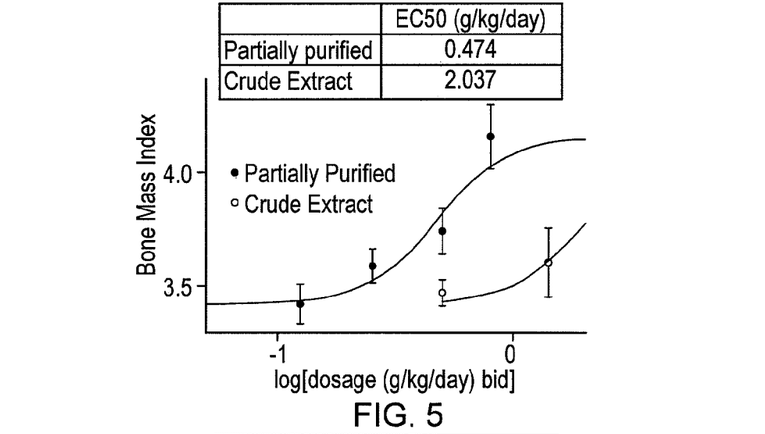
FIG. 5 is a graph illustrating the activities of the mixture (with and without partial purification) on the femoral bone mass index.

P < 0.05 compared to sham-operated normal control
P < 0.01 compared to sham-operated normal control
*P < 0.05 compared to ovariectomized model
**P < 0.01 compared to ovariectomized model Based on the data of femoral bone mass index, the dose-response curve can be best fitted with an ED50 value of 0.474 g/kg/day, dosed twice a day, as shown in FIG. 5. Compared to crude extract prepared as described in the document (GuMiAn Patent File A), the partially purified active components were about 4 times more potent.

FIG. 5 shows dose-response curves of partially purified active components (solid points) and crude extract (open circles) on the femoral bone mass index in ovariectomized osteoporosis animal model. All the values are expressed as mean±standard deviation. The data points were fitted with a non-linear regression program, GraphPad Prism version 3.00 for Windows, GraphPad Software, San Diego Calif. USA, www.graphpad.com.

We measured the bone mineral densities of femur and lumbar spine. The values were tabulated in Table 7. On BMD of femur, Fosamax® and partially purified active components at all dosages were statistically significant from the value of ovariectomized model group. However, on BMD values of lumbar spine, only groups dosed with Fosamax®, GuMiAn crude extract at 1.4 g/kg/day, and partially purified GuMiAn at 0.5 g/kg/day showed statistically difference as compared to the ovariectomized model group.

Figure 6:
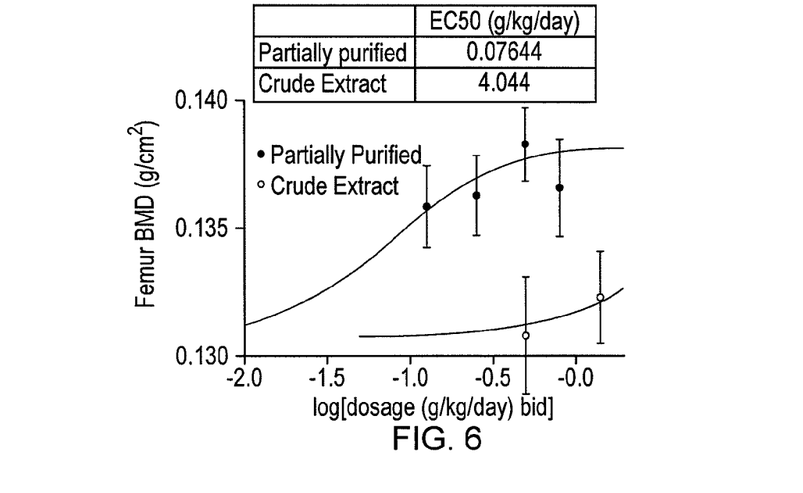
FIGS. 6 and 7 are dose response curves for the mixture (with and without partial purification) on bone mineral density in the femur (FIG. 6) and the lumbar spine (FIG. 7).
Figure 7:
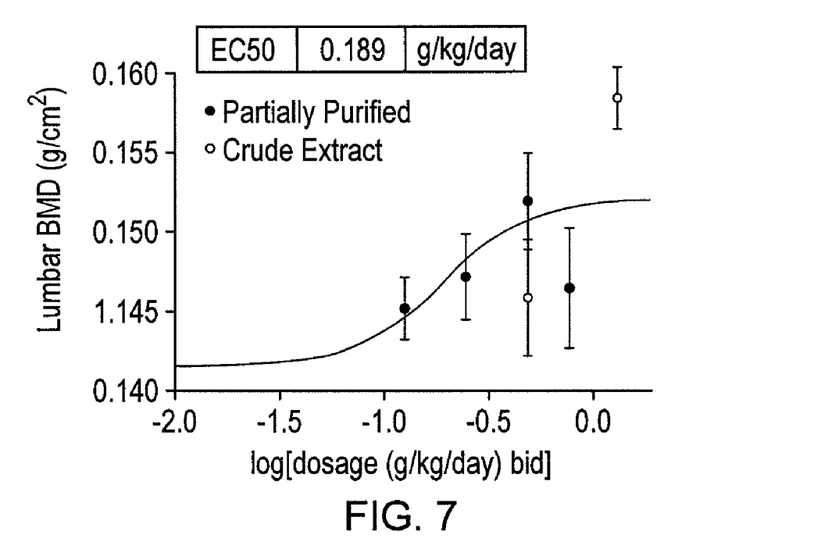

Dose response curves of GuMiAn crude extract and partially purified GuMiAn can be best fitted with a non-linear regression software program (FIG. 6 for femur and FIG. 7 for lumbar spine). Improvement in the potency in vivo is clearly indicated.

TABLE 7

Bone mineral densities of femur and lumbar spine from each experimental group.

| Groups | Rat # | Femur ($\bar{x} \pm s$) | Lumbar Spine ($\bar{x} \pm s$) |
|---|---|---|---|
| Sham-operated Normal Control | 12 | 0.1373 ± 0.00349 | 0.1497 ± 0.0544 |
| Ovariectomized Model | 12 | 0.1309 ± 0.00452# | 0.1415 ± 0.00425# |
| Fosamax ® | 10 | 0.1436 ± 0.00483** | 0.1610 ± 0.00774** |
| Crude Extract | | | |
| 1.4 g/kg | 11 | 0.1322 ± 0.00602 | 0.1581 ± 0.00627** |
| 0.5 g/kg | 10 | 0.1307 ± 0.00732 | 0.1456 ± 0.01165 |
| Partially Purified | | | |
| 0.12 g/Kg | 11 | 0.1358 ± 0.00536* | 0.1451 ± 0.00633 |
| 0.25 g/Kg | 11 | 0.1362 ± 0.00522* | 0.1470 ± 0.00897 |
| 0.5 g/Kg | 11 | 0.1382 ± 0.00477** | 0.1517 ± 0.01008** |
| 0.8 g/Kg | 6 | 0.1365 ± 0.00460* | 0.1462 ± 0.00939 |

P < 0.05 compared to sham-operated normal control
P < 0.01 compared to sham-operated normal control
*P < 0.05 compared to ovariectomized model
**P < 0.01 compared to ovariectomized model FIG. 6 shows dose-response curves of partially purified GuMiAn (solid points) and GuMiAn crude extract on the bone mineral density of femur in ovariectomized osteoporosis animal model. All the values are expressed as mean±standard deviation. The data points were fitted with a non-linear regression program, GraphPad Prism version 3.00 for Windows, GraphPad Software, San Diego Calif. USA, www.graphpad.com.

FIG. 7 shows dose-response curves of partially purified GuMiAn (solid points) and GuMiAn crude extract on the bone mineral density of lumbar spine in ovariectomized osteoporosis animal model. All the values are expressed as mean±standard deviation. The data points were fitted with a non-linear regression program, GraphPad Prism version 3.00 for Windows, GraphPad Software, San Diego Calif. USA, www.graphpad.com.

Obesity

The effects of the purified composition on the body weight of the rats in the groups described above were determined.

Figure 8:
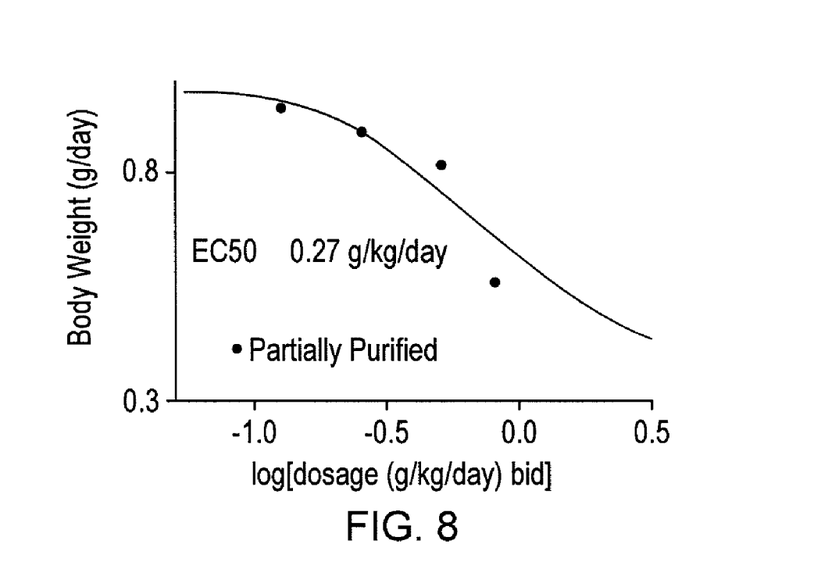
FIG. 8 is a graph relating dosage with the partially purified structure to change in body weight.

We measured the body weight of each experimental animal group weekly. The ovariectomized rats had been noticed to have a pronounced body weight increase compared to the sham-operated normal control group. Treatment of the ovariectomized animals with the partially purified composition showed a significant decrease in the body weight increment. FIG. 8 shows a plot of the average body weight increment of the treated animals with an ED50 of 0.27 g/kg/day.

The data points were fitted with a non-linear regression program, GraphPad Prism version 3.00 for Windows, GraphPad Software, San Diego Calif. USA, www.graphpad.com.

Human Studies

A pilot study has been carried out of the safety and efficacy of a composition according to the invention when administered to postmenopausal osteoporotic women.

For this study, the "crude extract" ("GZS") was formulated into capsules.

Methods

Women with osteoporosis as defined by the bone mineral density (BMD) score of <2.5 SD peak bone mass in either the hip and/or spine were enrolled in the study. All subjects are >5 years post menopause, up to the age of 70 years. The subjects gave informed consent. Subjects with renal, thyroid, parathyroid dysfunction, major disease, diabetic requiring insulin, and taking steroids, bisphosphonates, hormone replacement therapy, or calcitonin were excluded from the study.

The study is a randomized open-labeled trial, 18 weeks treatment, with a 9-month follow-up. Patients received either Ca et Vit D 2 tablets a day (control arm) or Ca et Vit D+GZS capsules (treatment arm).

Markers of bone formation: bone-specific alkaline phosphatase, and markers of bone resorption: urinary deoxy-pyridiolone, and urinary cross-linked N-telopeptide were assessed. BMD was assessed at baseline and at the end of the study.

Results 22 subjects were enrolled into the study, with 4 randomized into the control arm and 18 in the treatment arm. 18 subjects completed the study. 3 subjects in the active arm and 1 subject in the control arm withdrew respectively. There were no meaningful changes in the bone formation and resorption markers. The mean (+/−SD) changes in BMD in the control and treatment groups are as follows: hip −11.26 and −2.51 percent; and spine −3.80 and −3.82 percent respectively. There were no fractures in both groups. 7 patients complained of minor side effects with GZS capsules, like "heatiness", headache and bloatedness.

Conclusions

In postmenopausal osteoporotic women, the composition according to the invention appears to reduce the bone loss measured in the hips but not the spine in the 9-month study period. It appears to be safe with only minor side effects. Larger and longer-term studies are needed to confirm its efficacy in ameliorating bone loss.

References

Kim et al. 2003. Effects of Eucommiae Cortex on osteoblast-like cell proliferation and osteoclast inhibition: Arch of Pharm Research 26(11): 929-936.

Kuo, P. L., Hsu, Y. L., Chang, C. H. & Chang, J. K. 2005. Osthole-mediated cell differentiation through bone morphogenetic protein-2/p38 and extracellular signal-regulated kinase ½ pathway in human osteoblast cells. Journal of Pharmacology and Experimental Therapeutics 314: 1290-1299.

Oh, K. O., Kim, S. W., Kim, J. Y., Ko, S. Y., Hyun-Man Kim, H. M., Baek, J. H., Ryoo, H. M. & Kim, J. K. 2003. Effect of Rehmannia glutinosa Libosch extracts on bone metabolism. Clinica Chimica Acta 334:185-195.

Wang, D. W., Li, F. M. & Jiang, Z. M. 2001. Osteoblastic proliferation stimulating activity of Psoralea coryfolia extracts and two of its flavanoids. Planta Med 67: 748-749.

Xie, F., Wu, C. F., Lai, W. P., Yang, X. J., Cheung, P. Y., Yao, X. S., Laung, P. C. & Wong, M. S. 2005. The osteoprotective effect of Herba epimedii (HEP) extract in vivo and in vitro. Evidence-based complementary and Alternative Medicine 2(3): 353-361.

Xiong, Z., Wang, D; Xu, Y. & Li, F. 2003. Osteoblastic differentiation bioassay and its application to investigating the activity of fractions and compounds from Psoralea corylifolia L. Pharmazie. 2003; 58(12):925-928.

Lee, N. K., Sowa, H., Hinoi, E., Ferron, M., Ahn, J. D., Confavreux, C., Dacquin, R., Mee, P. J., McKee, M. D., Jung, D. Y., et al. (2007). Cell, 130, 456-469

Goulding, A., Jones, I. E., Taylor, R. W., Williams, S. M., and Manning, P. J. (2001). J. Pediatr. 139, 509-515.

Schwartz, A. V., Sellmeyer, D. E., Ensrud, K. E., Cauley, J. A., Tabor, H. K., Schreiner, P. J., Jamal, S. A., Black, D. M., Cummings, S. R., (2001). J. Clin. Endocrinol. Metab. 86, 32-38.

Gerdhem, P., Isaksson, A., Akesson, K., and Obrant, K. J. (2005). Osteoporos. Int. 16, 1506-1512.

Inaba, M. (2004). J. Bone Miner. Metab. 22, 287-292.

While the invention has been described above by reference to preferred embodiments, it will be understood by those skilled in the art that various changes and modifications may be made without departing from the spirit and scope of the invention. It is intended to cover all such changes and modifications by the appended claims.

The invention claimed is:

1. A pharmaceutical composition comprising the following six herbal materials: (i) purified extract of Yin Yang Huo; (ii) purified extract of Bu Gu Zhi; (iii) purified extract of Shu Di; (iv) purified extract of Du Zhong; (v) purified extract of She Chuang Zhi; and (vi) purified extract of Huang Qi, wherein component (i) is produced by fractionating an alcohol solvent extract of Yin Yang Huo by chromatography on silica gel, the active fraction being eluted using 20% methanol in ethyl acetate, then concentrated and dried in vacuum; wherein component (ii) is produced by fractionating alcohol solvent extract of Bu Gu Zhi by chromatography on a lipophilic crosslinked dextran-based resin using methanol as eluant, the eluted fraction being concentrated and evaporated to dryness under vacuum; wherein component (iii) is produced by adding ethanol to a crude aqueous extract of Shu Di and collecting the precipitate formed; wherein component (iv) is produced by fractionating an alcohol solvent extract of Du Zhong by chromatography on silica gel; wherein component (v) is produced by adding acetone to an alcohol solvent extract of She Chuang Zhi, collecting the acetone extract, followed by evaporation to dryness of the acetone extract; and wherein component (vi) is produced by adding ethanol to a water extract of Huang Qi and collecting the precipitate formed.

2. The composition of claim 1, wherein the proportion, in parts by weight of the six purified extracts, of Yin Yang Huo is 0.15-0.75 parts and Bu Gu Zhi is 1.5-6 parts.

3. A pharmaceutical composition according to claim 1 wherein the alcohol solvent extracts of (i) Yin Yang Huo, (ii) Bu Gu Zhi, (iv) Du Zhong and (v) She Chuang Zhi were produced by extraction with aqueous ethanol.

4. A pharmaceutical composition according to claim 3 wherein the aqueous ethanol is 70% aqueous ethanol.

5. A pharmaceutical composition according to claim 1 which contains purified extracts of said herbal materials in the proportion, in parts by weight of the six purified extracts, as follows:
(i) Yin Yang Huo: 0.15-0.75 parts;
(vi) Huang Qi: 0.3-1.5 parts;
(v) She Chuang Zhi: 1-4 parts;
(iii) Shu Di: 1.2-5.0 parts;
(ii) Bu Gu Zhi: 1.5-6 parts; and
(iv) Du Zhong: 2.5-10 parts.

6. A pharmaceutical composition according to claim 5 wherein the proportions are:
(i) 0.25-0.5 parts;
(vi) 0.5-1.0 parts;
(v) 1.2-2.8 parts;
(iii) 1.5-3.0 parts;
(ii) 2-4 parts; and
(iv) 4-8 parts.

7. A pharmaceutical composition according to claim 6 wherein the proportions are:
(i) 0.375 parts of Yin Yang Huo; (vi) 0.75 parts of Huang Qi;
(v) 2 parts of She Chuang Zhi; (iii) 2.5 parts of Shu Di
(ii) 3 parts of Bu Gu Zhi; and (iv) 5 parts of Du Zhong.

8. A pharmaceutical composition according to claim 1 including one or more excipients or adjuvants.

9. A pharmaceutical composition comprising the following six herbal materials: (i) purified extract of Yin Yang Huo; (ii) purified extract of Bu Gu Zhi; (iii) purified extract of Shu Di; (iv) purified extract of Du Zhong; (v) purified extract of She Chuang Zhi; and (vi) purified extract of Huang Qi, wherein component (i) is produced by fractionating an alcohol solvent extract of Yin Yang Huo by chromatography on silica gel, the active fraction being eluted using 20% methanol in ethyl acetate, then concentrated and dried in vacuum; wherein component (ii) is produced by fractionating alcohol solvent extract of Bu Gu Zhi by chromatography on a lipophilic crosslinked dextran-based resin using methanol as eluant, the eluted fraction being concentrated and evaporated to dryness under vacuum; wherein component (iii) is produced by adding ethanol to a crude aqueous extract of Shu Di and collecting the precipitate formed; wherein component (iv) is produced by fractionating an alcohol solvent extract of Du Zhong by chromatography on silica gel; wherein component (v) is produced by adding acetone to an alcohol solvent extract of She Chuang Zhi, collecting the acetone extract, followed by evaporation to dryness of the acetone extract; and wherein component (vi) is produced by adding ethanol to a water extract of Huang Qi and collecting the precipitate formed, wherein the proportion, in parts by weight of the six purified extracts, of Yin Yang Huo is 0.15-0.75 parts and Bu Gu Zhi is 1.5-6 parts.

* * * * *